United States Patent [19]

Anderson

[11] Plant 4,314

[45] Oct. 10, 1978

[54] NECTARINE TREE (48-G-140)

[75] Inventor: Frederic W. Anderson, Merced, Calif.

[73] Assignee: The Burchell Nursery, Inc., Modesto, Calif.

[21] Appl. No.: 867,372

[22] Filed: Jan. 6, 1978

[51] Int. Cl.[2] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is medium size, vigorous, upright to spreading, open, foliated with medium size, lanceolate, acutely pointed leaves having a crenate margin and alternate, reniform glands, blooms mid-season with large flowers, and is a regular and productive bearer of large to medium size, symmetrical, globose, freestone fruit having yellow skin substantially overspread with red, and yellow flesh with red next to the stone.

1 Drawing Figure

BACKGROUND OF THE VARIETY

1. Field of the Invention

Over a substantial number of years I have engaged in an extensive and continuing plant breeding program at my experimental nursery and orchard located near Le Grand, Merced County, California; one purpose of such program being to provide improved varieties of fruit trees. The present variety of nectarine tree resulted from my endeavors in the conduct of such plant breeding program; such variety being embraced by Class 41, Plants, of the United States Patent Office MANUAL OF CLASSIFICATION.

2. Prior Varieties

Among the existent varieties of nectarine trees which are known to me, I make particular reference to the Le Grand (U.S. Plant Pat. No. 549) mentioned hereinafter for the purpose of comparison.

ORIGIN OF THE VARIETY

The present variety of nectarine tree was originated by me, in my experimental nursery and orchard, located as aforesaid, as a cross between the Summer Grand (U.S. Plant Pat. No. 2,879) as the seed parent and May Grand (U.S. Plant Pat. 2,794) as the pollen parent. In maturity, such cross evidenced certain desirable characteristics for commercial production, and I, therefore, selected it for asexual reproduction.

ASEXUAL REPRODUCTION OF THE VARIETY

Subsequent to origination and selection by me of the present variety of nectarine tree, I asexually reproduced it by top-working on mature trees in my said experimental orchard, and—in maturity—such reproductions ran true to the original tree in all respects.

SUMMARY OF THE VARIETY

The herein-claimed new and distinct variety of nectarine tree is medium size, vigorous, upright to spreading, open, foliated with medium size, lanceolate, acutely pointed leaves having a crenate margin and alternate, reniform glands, blooms mid-season with large flowers, and is a regular and productive bearer of large to medium size, symmetrical, globose, freestone fruit having yellow skin substantially overspread with red, and yellow flesh with red next to the stone; the variety being particularly characterized, as to novelty, by fruit which—generally resembling the clingstone fruit of the Le Grand—is freestone, and ripens a few days later.

BRIEF DESCRIPTION OF THE DRAWING

The drawing is an illustration, by photographic reproduction in color, of a twig with leaves, and separate fruit; one of the latter being halved to show the flesh, and the stone remaining in one of the halves.

DESCRIPTION OF THE VARIETY

The botanical details of this new and distinct variety of nectarine tree—with color definitions (except those in common color terms) referenced to Maerz and Paul Dictionary of Color—are as follows:

TREE

Size: Medium.
Vigor: Vigorous.
Form: Upright to spreading.
Growth: Open.
Production: Productive.
Bearing: Regular bearer.

TRUNK

Size: Medium.
Texture: Medium.

BRANCHES

Size: Medium.
Texture: Medium.

LEAVES

Size: Medium
*Average length.*—6".
*Average width.*—$\frac{3}{4}$".
Form: Lanceolate. Acutely pointed.
Thickness: Medium.
Margin: Crenate.
Petiole: Medium length. Medium thickness.
Glands: Number and position — usually 2 on petiole and 2 on blade. Alternate. Medium size. Reniform.
Color:
*Top side.*—Medium green (23-L-8).
*Under side.*—Lighter green (22-L-7).

FLOWER BUDS

Size: Medium.

FLOWERS

Blooming period: Mid-season. Medium, as compared with other varieties.
Size: Large.

FRUIT

Maturity when described: Hard (Aug. 16, 1977).
Date of first picking: Aug. 16, 1977.
Date of last picking: Aug. 26, 1977.
Size: Large to medium. Uniform.
*Average diameter axially.*—$2\frac{1}{2}''$.
*Average transversely in suture plane.*—$2\frac{5}{8}''$.
Form: Uniform to variable. Symmetrical. Globose.
Suture: Distinct. Shallow. Extends from base to beyond apex, with slight depression beyond pistil point.
Ventral surface: Rounded strongly.
Cavity: Rounded. Elongated in suture plane, with suture showing on both sides.
Base: Rounded.
Apex: Short.
Pistil point: Wanting.

SKIN

Thickness: Medium.
Texture: Medium.
Tendency to crack: None noted.
Down: Wanting.
Color: Golden Glow yellow (9-L-6) substantially overspread with red (5-L-5) shading to darker red (7-L-5), with some mottling and streaking.

FLESH

Texture: Firm. Crisp. Meaty.
Fibers: Few.
Ripens: Evenly.
Aroma: Wanting.
Flavor: Subacid.
Eating quality: Good.
Color: Yellow (10-L-5) with red next to stone.

*Surface of pit cavity.*—Red (5-L-5) with white fibers.

STONE

Type: Free.
Size: Medium.
*Average length.*—$1\frac{1}{4}''$.
*Average breadth.*—$1\frac{1}{4}''$.
*Average thickness.*—$\frac{7}{8}''$.
Form: Oblong — obovoid.
Base: Straight.
Apex. Rounded.
Sides: Equal.
Ridges: Jagged.
Tendency to split: Slight.
Color: Cattail brown (8-H-12).

USE

Market: local. Dessert. Long distance shipping.

KEEPING QUALITY

Good.

RESISTANCE TO INSECTS AND DISEASES

No unusual susceptibilities noted.

SHIPPING QUALITY

Good.

The nectarine tree and its fruit herein described may vary in slight detail due to climatic and soil conditions under which the variety may be grown; the present description being of the variety as grown in the Central Valley of Calif.

I claim:

1. A new and distinct variety of nectarine tree, substantially as illustrated and described, characterized by fruit having general resemblance to the clingstone fruit of the Le Grand nectarine, but bearing freestone fruit, and ripening a few days later.

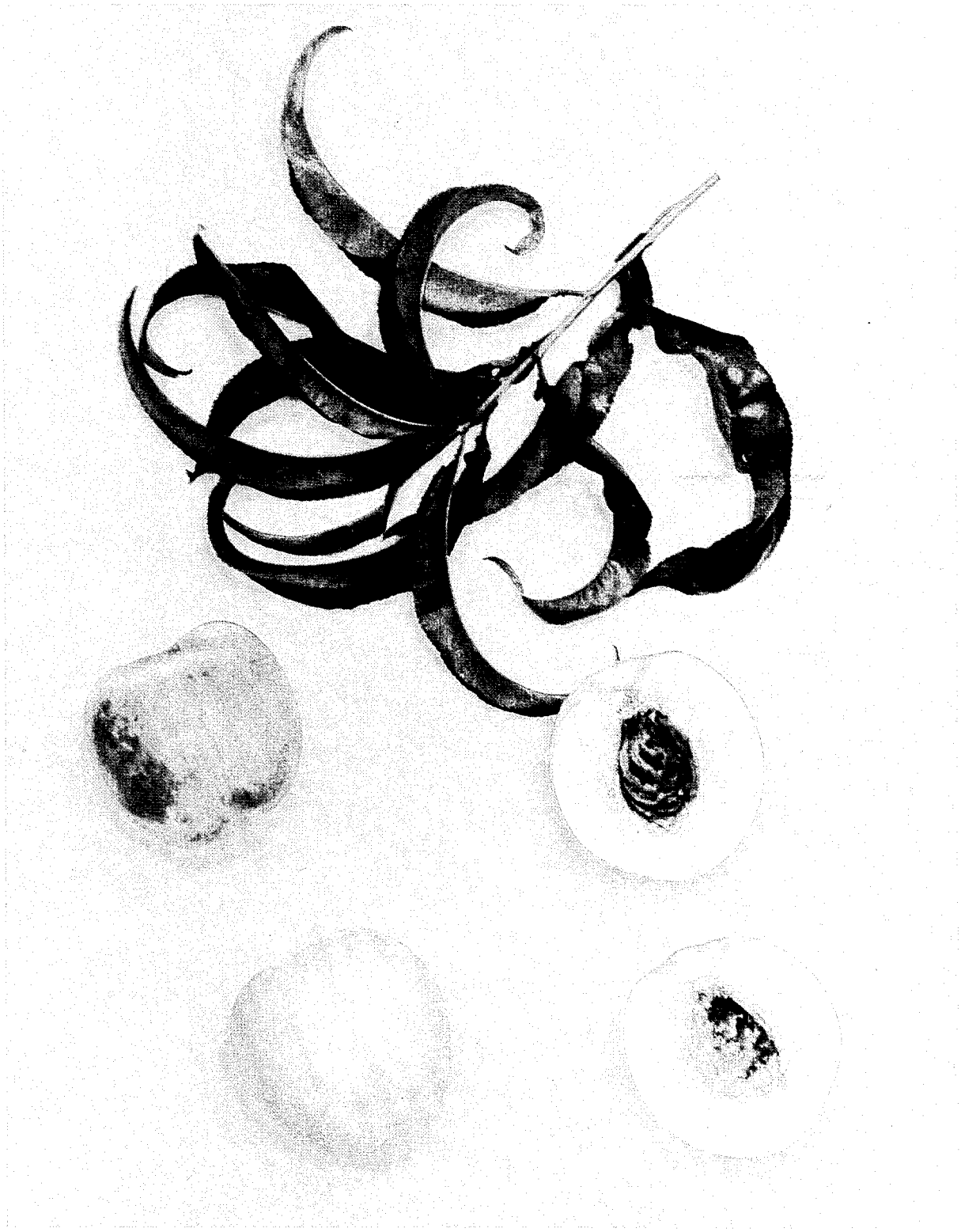

* * * * *